(12) United States Patent
Runfola

(10) Patent No.: US 7,846,135 B2
(45) Date of Patent: Dec. 7, 2010

(54) RETRACTABLE NEEDLE SYRINGE WITH NEEDLE TRAP

(75) Inventor: Vincent Runfola, Apopka, FL (US)

(73) Assignee: Midland Medical Holding LLC

( * ) Notice: Subject to any disclaimer, the term of this patent is extended or adjusted under 35 U.S.C. 154(b) by 112 days.

(21) Appl. No.: 11/677,721

(22) Filed: Feb. 22, 2007

(65) Prior Publication Data

US 2008/0021389 A1 Jan. 24, 2008

Related U.S. Application Data

(60) Provisional application No. 60/776,206, filed on Feb. 24, 2006.

(51) Int. Cl.
*A61M 5/00* (2006.01)
*A61M 5/32* (2006.01)
(52) U.S. Cl. ...................... 604/195; 604/110
(58) Field of Classification Search ............... 604/110, 604/192–198, 207, 218, 222, 228
See application file for complete search history.

(56) References Cited

U.S. PATENT DOCUMENTS

| | | |
|---|---|---|
| 2,722,215 A | 11/1955 | Dahlgren |
| 3,669,111 A | 6/1972 | Dubner |
| 3,797,489 A | 3/1974 | Sarnoff |
| 4,542,749 A | 9/1985 | Caselgrandi et al. |
| 4,553,962 A | 11/1985 | Brunet |
| 4,650,468 A | 3/1987 | Jennings, Jr. |
| 4,747,829 A | 5/1988 | Jacob et al. |
| 4,747,830 A | 5/1988 | Gloyer et al. |
| 4,747,831 A | 5/1988 | Kulli |
| 4,804,370 A | 2/1989 | Haber et al. |
| 4,808,169 A | 2/1989 | Haber et al. |
| 4,813,940 A | 3/1989 | Parry |
| 4,820,275 A | 4/1989 | Haber et al. |
| 4,826,484 A | 5/1989 | Haber et al. |
| 4,826,489 A | 5/1989 | Haber et al. |
| 4,834,718 A | 5/1989 | McDonald |

(Continued)

FOREIGN PATENT DOCUMENTS

CA 2338830 A1 3/2000

(Continued)

*Primary Examiner*—Matthew F DeSanto
(74) *Attorney, Agent, or Firm*—Robert C. Klinger

(57) ABSTRACT

A syringe includes a hollow barrel and a hollow plunger extending into the barrel and being axially movable within the barrel, where the plunger includes an end wall that is releasably secured to the plunger at an opening disposed at a distal end of the plunger and is movable to disengage with the plunger distal end opening during use of the syringe to facilitate access to a retraction cavity disposed within the plunger. A needle assembly is secured within and at a distal end of the barrel. The needle assembly includes a needle holder with a connector to secure a needle to the needle holder. The needle holder is biased toward the proximal end of the barrel and is configured to be forced into the retraction cavity of the plunger upon complete depression of the plunger distally within the barrel, and the plunger includes at least one protrusion that extends from an internal wall surface of the plunger within the retraction cavity and is configured to engage with and limit or prevent movement of portions of the needle assembly that have been forced into the retraction cavity.

21 Claims, 11 Drawing Sheets

U.S. PATENT DOCUMENTS

| | | | |
|---|---|---|---|
| 4,838,869 A | 6/1989 | Allard | |
| 4,838,870 A | 6/1989 | Haber et al. | |
| 4,842,587 A | 6/1989 | Poncy | |
| 4,846,808 A | 7/1989 | Haber et al. | |
| 4,850,374 A | 7/1989 | Diaz-Ramos | |
| 4,861,338 A | 8/1989 | Mathiesen et al. | |
| 4,874,382 A | 10/1989 | Lindemann et al. | |
| 4,883,471 A | 11/1989 | Braginetz et al. | |
| 4,904,242 A | 2/1990 | Kulli | |
| 4,908,022 A | 3/1990 | Haber | |
| 4,909,794 A | 3/1990 | Haber et al. | |
| 4,915,699 A | 4/1990 | Kornberg | |
| 4,915,700 A | 4/1990 | Noonan, Jr. | |
| 4,919,652 A | 4/1990 | Alter et al. | |
| 4,921,486 A | 5/1990 | DeChellis et al. | |
| 4,931,040 A | 6/1990 | Haber et al. | |
| 4,932,939 A | 6/1990 | Magre et al. | |
| 4,935,014 A | 6/1990 | Haber | |
| 4,935,015 A | 6/1990 | Hall | |
| 4,935,016 A | 6/1990 | Deleo | |
| 4,941,883 A | 7/1990 | Venturini | |
| 4,944,723 A | 7/1990 | Haber et al. | |
| 4,944,725 A | 7/1990 | McDonald | |
| 4,950,241 A | 8/1990 | Ranford | |
| 4,950,251 A | 8/1990 | Haining | |
| 4,955,870 A | 9/1990 | Ridderheim | |
| 4,957,490 A | 9/1990 | Byrne et al. | |
| 4,966,593 A | 10/1990 | Lennox | |
| 4,978,340 A | 12/1990 | Terrill et al. | |
| 4,986,813 A | 1/1991 | Blake, III et al. | |
| 4,994,034 A | 2/1991 | Botich et al. | |
| 4,995,874 A | 2/1991 | Strickland | |
| 5,019,044 A | 5/1991 | Tsao | |
| 5,030,208 A | 7/1991 | Novacek et al. | |
| 5,049,133 A | 9/1991 | Villen Pascual | |
| 5,053,010 A | 10/1991 | McGary et al. | |
| 5,064,419 A | 11/1991 | Gaarde | |
| 5,084,029 A | 1/1992 | Nacci nee' Tagliaferri et al. | |
| 5,085,638 A | 2/1992 | Farbstein et al. | |
| 5,090,962 A | 2/1992 | Landry, Jr. et al. | |
| 5,112,316 A | 5/1992 | Venturini | |
| 5,120,310 A | 6/1992 | Shaw | |
| 5,122,118 A | 6/1992 | Haber et al. | |
| 5,122,124 A | 6/1992 | Novacek et al. | |
| 5,125,898 A | 6/1992 | Kaufhold, Jr. et al. | |
| 5,163,918 A | 11/1992 | Righi et al. | |
| 5,180,369 A | 1/1993 | Dysarz | |
| 5,180,370 A * | 1/1993 | Gillespie | 604/110 |
| 5,188,599 A | 2/1993 | Botich et al. | |
| 5,188,613 A | 2/1993 | Shaw | |
| 5,201,710 A | 4/1993 | Caselli | |
| 5,205,826 A | 4/1993 | Chen | |
| 5,211,628 A | 5/1993 | Marshall | |
| 5,242,402 A | 9/1993 | Chen | |
| 5,267,961 A | 12/1993 | Shaw | |
| 5,304,138 A | 4/1994 | Mercado | |
| 5,308,331 A | 5/1994 | Avila et al. | |
| 5,328,484 A | 7/1994 | Somers et al. | |
| 5,370,620 A | 12/1994 | Shonfeld | |
| 5,376,080 A | 12/1994 | Petrussa | |
| 5,380,295 A | 1/1995 | Vacca | |
| 5,385,551 A | 1/1995 | Shaw | |
| 5,389,076 A | 2/1995 | Shaw | |
| 5,401,246 A | 3/1995 | Mazur et al. | |
| 5,407,431 A | 4/1995 | Botich et al. | |
| 5,407,436 A | 4/1995 | Toft et al. | |
| 5,423,758 A | 6/1995 | Shaw | |
| 5,533,970 A | 7/1996 | Berger et al. | |
| 5,578,011 A | 11/1996 | Shaw | |
| 5,632,733 A | 5/1997 | Shaw | |
| 5,637,092 A | 6/1997 | Shaw | |
| 5,779,679 A | 7/1998 | Shaw | |
| 5,782,804 A | 7/1998 | McMahon | |
| 5,810,775 A | 9/1998 | Shaw | |
| 5,817,058 A | 10/1998 | Shaw | |
| 5,882,342 A | 3/1999 | Cooper et al. | |
| 5,935,104 A | 8/1999 | Janek et al. | |
| 5,984,898 A | 11/1999 | Garvin | |
| 5,989,220 A | 11/1999 | Shaw et al. | |
| 5,997,512 A | 12/1999 | Shaw | |
| 6,015,438 A | 1/2000 | Shaw | |
| 6,074,370 A * | 6/2000 | Pressly et al. | 604/195 |
| 6,090,077 A | 7/2000 | Shaw | |
| 6,096,005 A | 8/2000 | Botich et al. | |
| 6,099,500 A | 8/2000 | Dysarz | |
| 6,156,013 A * | 12/2000 | Mahurkar | 604/195 |
| 6,179,812 B1 | 1/2001 | Botich et al. | |
| 6,210,371 B1 | 4/2001 | Shaw | |
| 6,221,055 B1 | 4/2001 | Shaw et al. | |
| 6,228,054 B1 | 5/2001 | Dysarz | |
| 6,241,707 B1 | 6/2001 | Dysarz | |
| 6,409,701 B1 | 6/2002 | Cohn et al. | |
| 6,413,237 B1 | 7/2002 | Caizza et al. | |
| 6,432,087 B1 | 8/2002 | Hoeck et al. | |
| 6,454,745 B1 | 9/2002 | Donnan et al. | |
| 6,494,863 B1 | 12/2002 | Shaw et al. | |
| 6,524,278 B1 | 2/2003 | Campbell et al. | |
| 6,558,357 B1 | 5/2003 | Hoeck | |
| 6,572,584 B1 | 6/2003 | Shaw et al. | |
| 6,585,690 B1 | 7/2003 | Hoeck et al. | |
| 6,599,268 B1 | 7/2003 | Townsend et al. | |
| 6,620,136 B1 | 9/2003 | Pressly, Sr. et al. | |
| 6,626,418 B2 | 9/2003 | Kiehne | |
| 6,626,863 B1 | 9/2003 | Berler | |
| 6,679,863 B2 | 1/2004 | Bush et al. | |
| 6,689,106 B2 | 2/2004 | Bush et al. | |
| 6,800,066 B2 | 10/2004 | Targell | |
| 6,872,193 B2 | 3/2005 | Shaw et al. | |
| 6,942,652 B1 | 9/2005 | Pressly, Sr. et al. | |
| 6,958,055 B2 | 10/2005 | Donnan et al. | |
| 6,991,215 B2 | 1/2006 | Kiehne | |
| 6,994,690 B2 | 2/2006 | Kiehne | |
| 7,001,364 B1 | 2/2006 | Farhi | |
| 7,014,622 B1 | 3/2006 | Pressly, Sr. et al. | |
| 7,018,344 B2 | 3/2006 | Bressler et al. | |
| RE39,107 E | 5/2006 | Shaw | |
| 7,090,656 B1 | 8/2006 | Botich et al. | |
| 7,104,400 B2 | 9/2006 | Kiehne | |
| 7,147,621 B2 * | 12/2006 | Kiehne | 604/110 |
| 2002/0161337 A1 | 10/2002 | Shaw et al. | |
| 2003/0023205 A1 | 1/2003 | Botich et al. | |
| 2003/0083621 A1 | 5/2003 | Shaw et al. | |
| 2004/0116857 A1 | 6/2004 | Kiehne | |
| 2004/0138619 A1 | 7/2004 | Kiehne | |
| 2004/0254540 A1 | 12/2004 | Shaw et al. | |
| 2005/0054980 A1 | 3/2005 | Targell | |
| 2005/0075606 A1 | 4/2005 | Botich et al. | |
| 2005/0131350 A1 | 6/2005 | Shaw et al. | |
| 2006/0084919 A1 | 4/2006 | Shaw et al. | |
| 2006/0100650 A1 | 5/2006 | Kiehne | |
| 2006/0108555 A1 | 5/2006 | Kiehne | |
| 2006/0189935 A1 | 8/2006 | Janek et al. | |
| 2006/0258984 A1 | 11/2006 | Kiehne | |
| 2007/0083166 A1 | 4/2007 | Botich et al. | |

FOREIGN PATENT DOCUMENTS

| | | |
|---|---|---|
| CH | 669910 | 4/1989 |
| WO | 8900432 | 1/1989 |
| WO | 8900435 | 1/1989 |
| WO | 8904681 | 6/1989 |
| WO | 9107199 | 5/1991 |
| WO | 9205818 | 4/1992 |
| WO | 2004060451 A1 | 7/2004 |

| WO | 2006044010 A2 | 4/2006 |
| WO | 2006044010 A3 | 4/2006 |
| WO | 2006119537 A1 | 11/2006 |
| WO | 2006119551 A1 | 11/2006 |
| WO | 2007028195 A1 | 3/2007 |

* cited by examiner

RETRACTABLE NEEDLE SYRINGE WITH NEEDLE TRAP

CROSS REFERENCE TO RELATED APPLICATIONS

This application claims priority from U.S. Provisional Patent Application Ser. No. 60/776,206, entitled "Retractable Needle Syringe With Needle Trap", and filed Feb. 24, 2006, the disclosure of which is incorporated herein by reference in its entirety.

FIELD

The present disclosure pertains to safety medical syringes and, in particular, to syringes including a needle that retracts and is limited to a single use.

BACKGROUND

Retractable syringes have become increasingly important and desirable for use in hospitals and medical facilities for a number of reasons. In particular, retractable syringes are typically limited to a single use, where the hypodermic needle of the syringe is withdrawn into the syringe after aspiration and injection of a fluid, thus preventing multiple uses of the syringe and the potential transmission of human immunodeficiency virus (HIV) as well as other diseases from patient-to-patient. The retraction of the needle within the syringe after use also shields the needle and prevents inadvertent needle jabs or pricks from occurring to patients and health care providers.

A variety of different retractable syringe devices have been designed to effectively withdraw the needle within the syringe after a single use. However, the challenge exists to design a retractable syringe that is limited to a single use yet is simplistic in design and assembly, such that the syringe can be produced on a large production scale while minimizing manufacturing costs.

A number of single use retractable syringes are known in the art including, without limitation, devices described in U.S. Pat. Nos. 5,578,011, 5,632,733, 6,090,077, and 5,935,104, the disclosures of which are incorporated herein by reference in their entireties. Additional embodiments of retractable needle syringes are also described in co-pending U.S. patent application Ser. No. 11/249,741, the disclosure of which is incorporated herein by reference in its entirety.

In retractable syringes such as the types described above, the syringe needle is typically withdrawn or retracted into a cavity within the plunger of the syringe after a single use. A resilient biasing member, such as a coil spring, is typically utilized to force the needle into the plunger after use. It would be beneficial to enhance operation of the syringe by controlling the force and velocity at which the needle is retracted within the plunger cavity as well as ensure the needle does not inadvertently escape from the plunger cavity once it has retracted within the plunger.

SUMMARY

In accordance with the present invention, a hollow plunger is provided for use in a retractable syringe, where the syringe comprises a hollow barrel including an opening at a proximal end of the barrel, an opening at a distal end of the barrel and a fluid chamber disposed within the barrel, and a needle assembly secured within and at a distal end of the barrel, the needle assembly including a needle holder with a connector to secure a needle to the needle holder so as to permit the needle to extend through the distal end opening of the barrel. The plunger is configured to extend into and axially move within the barrel toward and away from the barrel distal end, and the plunger further comprises an end wall that is releasably secured to the plunger at an opening disposed at a distal end of the plunger and is movable to disengage with the plunger distal end opening during use of the syringe to facilitate access to a retraction cavity disposed within the plunger, where the needle holder is biased toward the proximal end of the barrel and is configured to be forced into the retraction cavity of the plunger upon complete depression of the plunger distally within the barrel. In addition, the plunger comprises at least one protrusion that extends from an internal wall surface of the plunger within the retraction cavity and is configured to engage with and limit or prevent movement of portions of the needle assembly that have been forced into the retraction cavity.

The above and still further objects, features and advantages of the present invention will become apparent upon consideration of the following detailed description of a specific embodiment thereof, particularly when taken in conjunction with the accompanying drawings wherein like reference numerals in the various figures are utilized to designate like components.

DETAILED DESCRIPTION

Embodiments of retractable syringes are described herein, where the syringes include a feature in which the syringe needle retracts within a retraction cavity of the plunger after use and is further trapped and prevented from removal from the plunger due to trapping structure disposed within the plunger retraction cavity.

Figure 1:
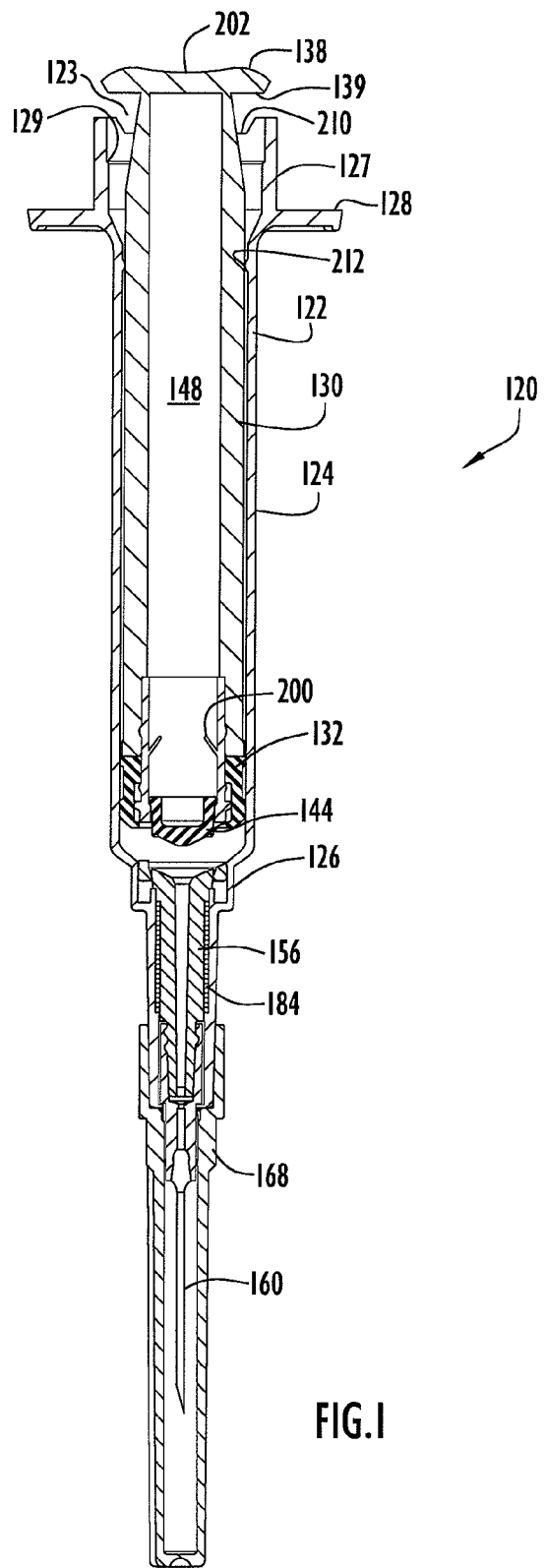
FIG. 1 is a side view in cross-section of a syringe in accordance with an embodiment of the present invention, where the needle extends from the syringe barrel and the syringe is ready for use.

An exemplary embodiment of a retractable syringe is depicted in FIGS. 1-7. Referring to FIG. 1, a medical syringe 120 includes a hollow cylindrical barrel 122 with an opening 123 at its proximal end and suitably dimensioned to receive a hollow plunger 130. The barrel further includes an opening at its distal end to permit exposure of a needle 160 from the syringe. The barrel 122 includes a main body portion 124 that receives and retains a portion of the plunger 130 and a distal end extension 126 of reduced internal diameter in relation to the main body portion 124 that receives a needle assembly 156 as described below. At least one bump or ridge 212 is disposed along an interior surface wall portion of the main body portion 124 within and near the proximal end of the barrel to resist or prevent complete removal of the plunger from the barrel during operation of the syringe. For example, the ridge could be continuous (e.g., forming a protruding annular ring) within the barrel. Alternatively, a series (e.g., two or more) of ridges can be provided at radially spaced locations along the interior barrel surface.

The plunger 130 includes a resilient seal 132 encircling the plunger near its distal end. The resilient seal 132 includes a distal end portion that extends over the plunger distal end in a manner as described below. A fluid cavity 150 is defined within the barrel 122 between the resilient seal 132 and other distal end portions of the plunger and a distal end 125 of the barrel main body portion 124, where the fluid cavity varies in volume based upon axial displacements of the plunger with respect to the barrel. A sheath 168 is removably secured to the distal end of the barrel 122 to enclose needle 160 secured within the barrel prior to use of the syringe. The barrel, plunger, resilient seal, sheath and all other components of the syringe may be constructed of any suitable medical grade materials (e.g., plastics, rubber materials, suitable metal materials such as stainless steels, etc.) that facilitate operability of the syringe as described below. Further, the syringe can be designed with a suitable fluid cavity to meet any fluid volume capacity for a particular application (e.g., 1 cubic centimeter or cc, 3 cc, 5 cc, etc.).

The proximal end of plunger 130 includes a thumb pad 138 and a radially extending flange 139 that facilitates engagement with the fingers and/or thumb of the user during operation of the syringe. In addition, the top surface of the thumb pad 138 includes a concave surface 202 to provide enhanced thumb or finger gripping action when the plunger is depressed within the barrel. The main body portion 124 of the barrel also includes a radially extending flange 128 disposed near its proximal end for facilitating engagement with the fingers and/or thumb of the user during operation. An extended barrel portion 127 extends between flange 128 and the proximal end of the barrel and is slightly greater in internal diameter in comparison to the remainder of main body portion 124. The extended barrel portion 127 is also of a sufficient longitudinal dimension, and is slightly smaller in internal diameter than the transverse dimension of the plunger defined at the flange 139, such that, when plunger 130 is fully depressed within the barrel, plunger flange 139 forces a slight flexure of the extended barrel portion 127 at the proximal end of the barrel to permit the flange to enter the extended barrel portion.

Two diametrically opposed sections are removed from extended barrel portion 127, so as to form cut-out areas or portions 210 along the extended barrel periphery. The cut-out portions 210 facilitate exposure of sufficient portions of the plunger thumb pad 138 and flange 139 to assist the user of the syringe in gripping the plunger when the plunger is pulled from the barrel to initiate aspiration of fluid within the fluid cavity of the barrel as described below. While two cut-out sections are depicted, it is noted that any suitable number of cut-out sections can be provided (e.g., one or more) at any one or more selected locations along the extended barrel portion. Preferably, the extended barrel portion wall thickness and/or plastic or other materials from which this portion is formed are selected to facilitate a slight elastic and reversible deformation of the extended barrel portion when grasped by a user so as to further assist in axially displacing a portion of the plunger from the barrel during aspiration of fluid into the barrel.

An annular groove 129 is disposed along remaining interior wall sections (i.e., the wall sections that are separated by the cut-out sections) of the extended barrel portion near the proximal end of the barrel. Upon complete depression of the plunger within the barrel and retraction of the syringe within the plunger, the plunger flange 139 engages in a snap-tight locking relationship with annular groove 129 to prevent removal of the plunger from the barrel. Alternatively, it is noted that the plunger and barrel can include any other suitable structure disposed at or near their proximal ends, distal ends and/or any other locations along each member that facilitate locking and preventing removal of the plunger from the barrel after a single use of the syringe.

Figure 2:
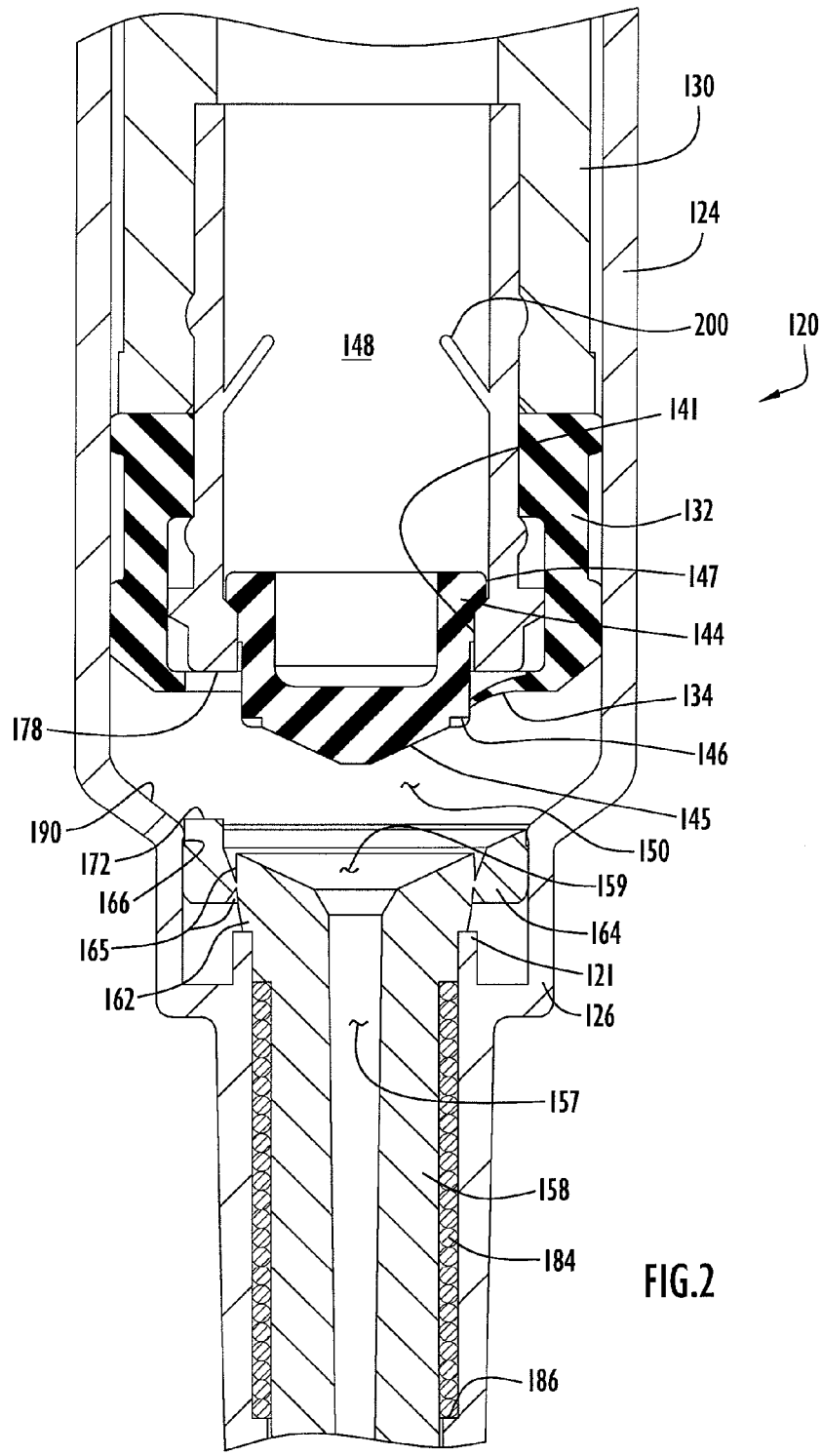
FIGS. 2-5 are partial side views in cross-section of the syringe of FIG. 1 detailing interaction of the distal end of the plunger and the proximal end of the needle assembly at varying stages of depression of the plunger to facilitate retraction of the needle assembly into the syringe in accordance with the present invention.
Figure 3:
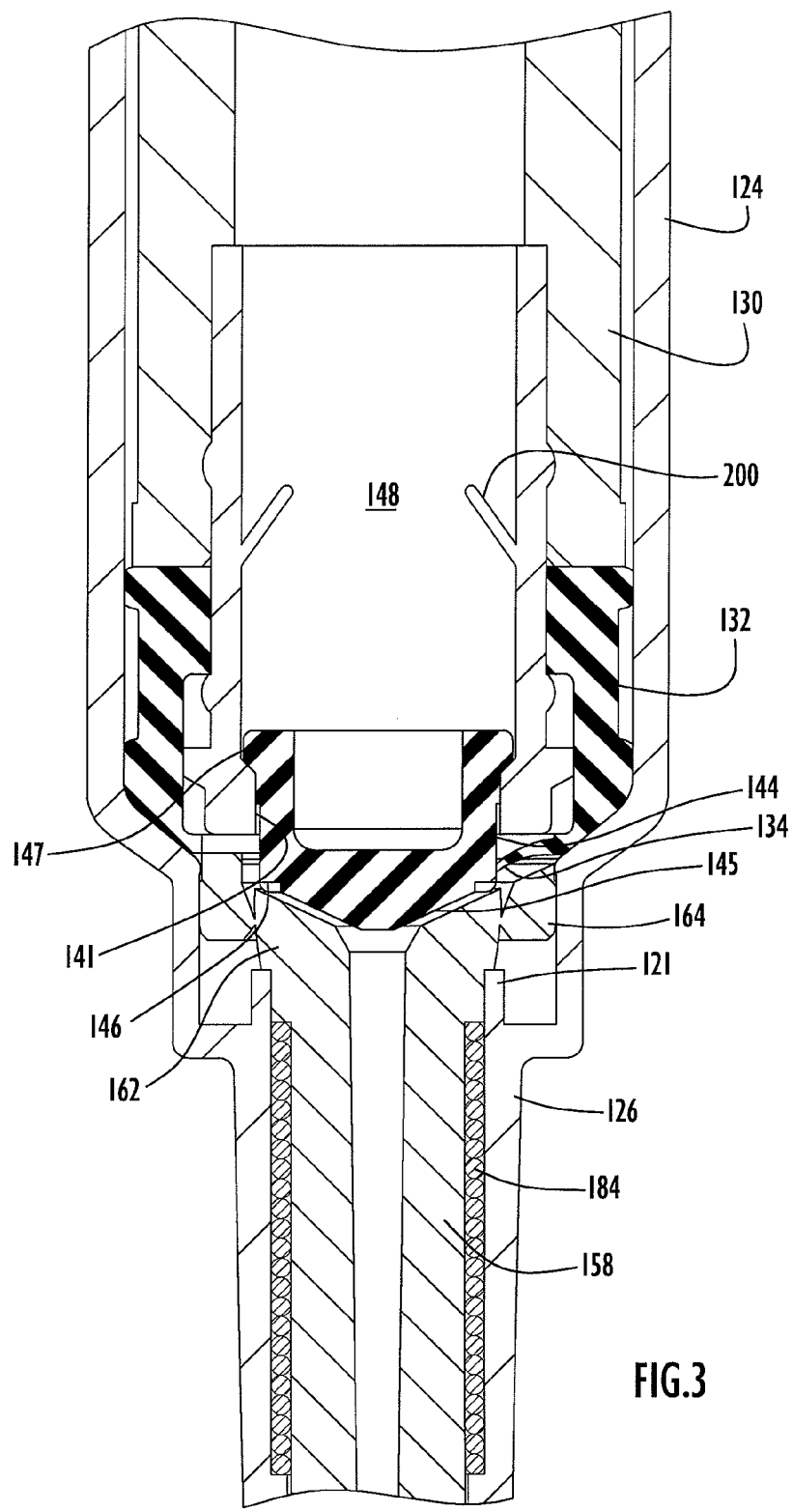
Figure 4:
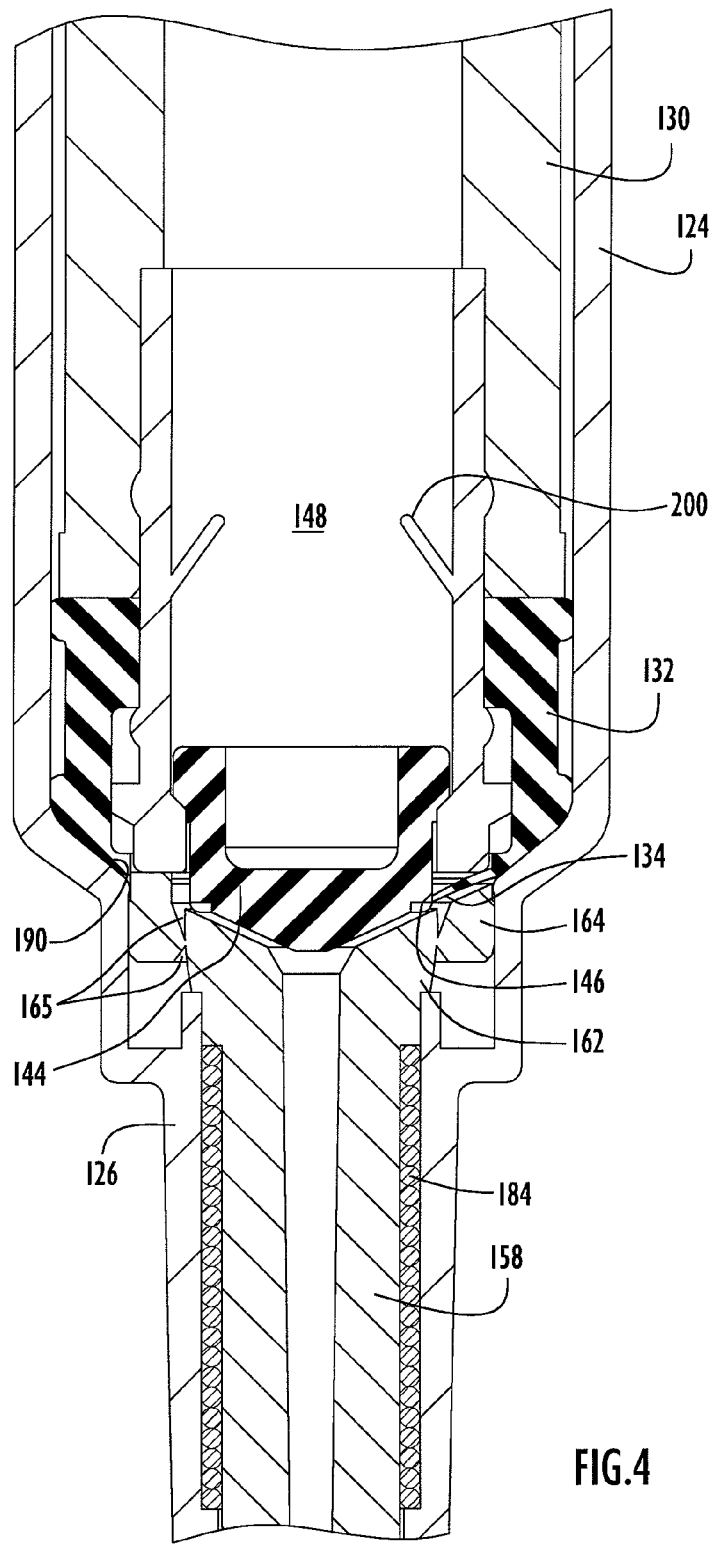
Figure 5:
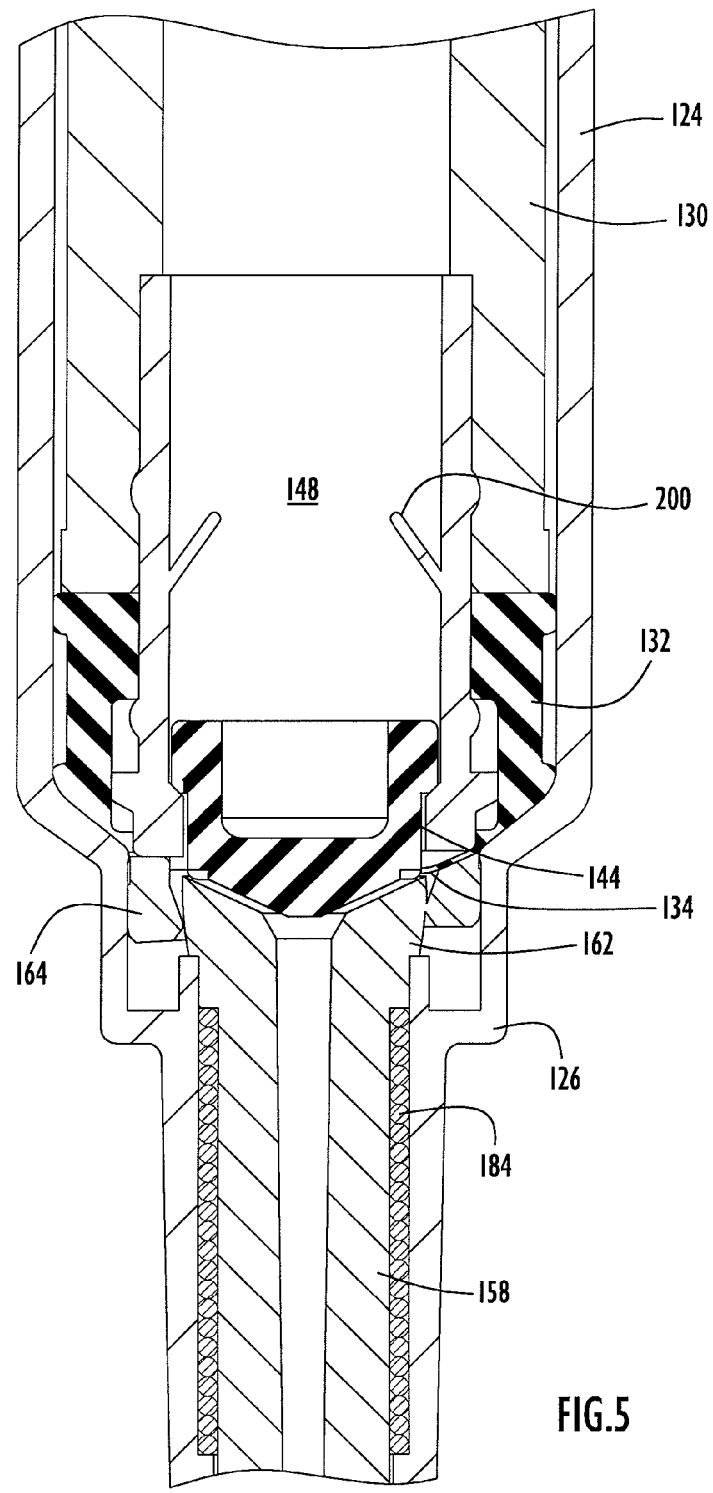

Referring to FIG. 2, a membrane or plug 144 is secured at the distal end of the plunger and is frictionally held between interior distal end wall portions of the plunger. The plug 144 seals the hollow interior or retraction cavity 148 of plunger 130, with the frictional engagement between the plug and the plunger being suitable to maintain engagement of the plug with the plunger until retraction of the needle assembly occurs as described below. Alternatively, it is noted that the plunger membrane or plug can be secured at the distal end of the plunger in a snap tight fitting relationship or in any other suitable manner.

As can be seen in FIG. 2, the distal end of plunger 130 includes an opening that communicates with retraction cavity 148 and into which plug 144 is secured. The interior annular wall at the distal end of the plunger includes an inwardly extending radial ledge 141. The diameter or transverse cross-section of the plunger opening, as defined at the ledge 141, is smaller than the diameter or transverse cross-section of the retraction cavity 148 that is defined within the plunger and lies beyond the ledge 141. Similarly, plug 144 includes an extending portion 147 that extends transversely from a proximal end of the plug. The extending portion 147 of the plug 144 is slightly larger in transverse cross-sectional dimension than the transverse cross-sectional dimension of the plunger opening defined at the ledge 141, so as to facilitate frictional contact between the ledge 141 and the extending portion 147 of the plug 144. The transverse cross-sectional dimensions of the extending portion 147 as well as the rest of the plug 144 are smaller than the transverse cross-sectional dimension of the retraction cavity 148 between the plunger ledge 141 and the proximal end of the plunger. Further, the transverse cross-sectional dimension of the remaining plug portion that extends between the extending portion 147 and the distal end of the plug 144 is slightly smaller than the transverse cross-sectional dimension of the plunger opening. Thus, upon axial displacement of the extending portion 147 of the plug 144 from the ledge 141 of the plunger 130 during retraction of the needle assembly, the frictional engagement between the plunger and the plug is released and the plug is free to move into the retraction cavity.

The resilient seal 132 includes one or more flaps 134 that extend beyond the distal end of the plunger and engage portions of the plunger plug 144 extending from the plug distal end when the plug is secured at the plunger distal end opening. The flaps 134 are flexible and biased to flex radially inward when the plug is displaced from the plunger distal end opening during retraction of the needle holder and needle within the plunger retraction cavity as described below.

Figure 7:
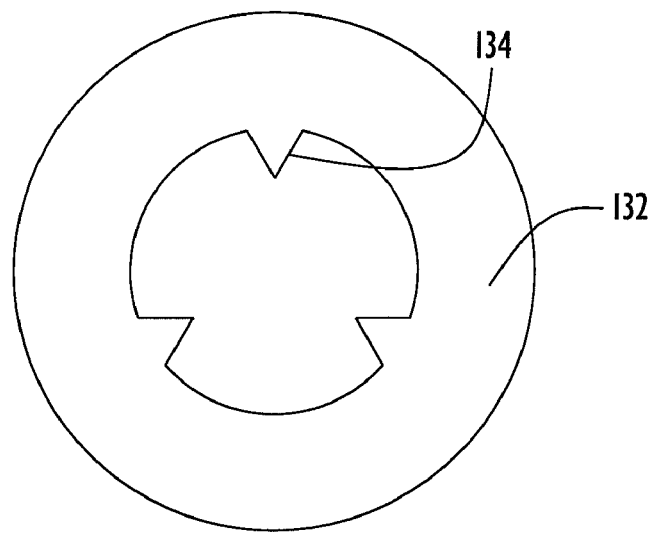
FIG. 7 is a distal end view of the plunger and resilient seal for the syringe of FIG. 1 with the plunger plug being retracted within the retraction cavity.

Referring to FIG. 7, the distal ends of the resilient seal and plunger are shown with the plunger plug removed from the distal end opening of the plunger (e.g., the plunger plug has been retracted within the plunger retraction cavity). As can be seen in this figure, three flaps 134 extend radially inward at the resilient seal distal end so as to cover portions of the plunger distal end opening. The three flaps 134 are angularly spaced at substantially equidistant locations from each other (e.g., each flap being angularly spaced about 120° from the flaps on either side of the flap).

The flaps of the resilient seal are further sufficiently flexible to flex inward slightly within the plunger distal end opening when portions of the needle assembly are retracted within the plunger in the manner described below. However, the bias of the flaps forces the flaps to resume the relaxed position as shown in FIG. 7, where the flaps extend radially inward from the resilient seal to partially cover the plunger distal end opening, upon movement of the needle assembly components beyond the flaps and into the retraction cavity of the plunger. In the relaxed position, the flaps partially cover and provide an obstruction at the plunger distal end opening so as to resist or prevent withdrawal or removal of the needle assembly components from the plunger after having been retracted into the plunger retraction cavity.

Figure 8:
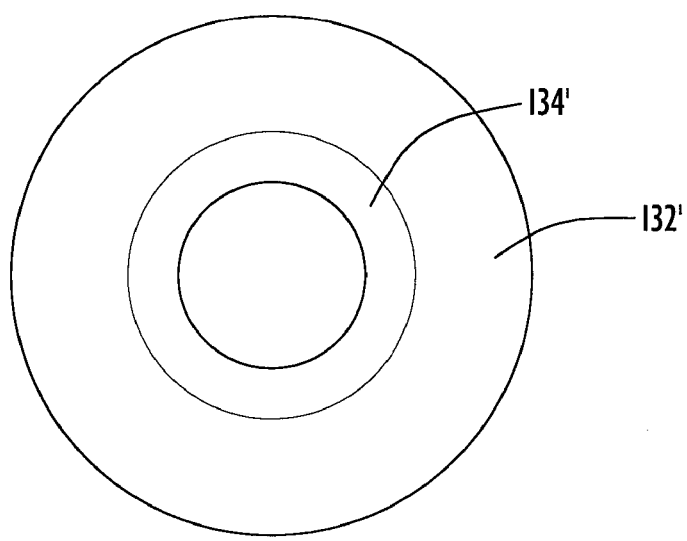
FIG. 8 is a distal end view of the plunger including an alternative embodiment of the resilient seal for the syringe of FIG. 1 with the plunger plug being retracted within the retraction cavity.

It is noted that the spacing and/or number of flaps for the resilient seal can be different from the configuration shown in FIG. 7 while providing the same or similar functional features. For example, the resilient seal can include a single flap or two or more flaps at any suitable spacing from each other. An alternative embodiment is shown, for example, in FIG. 8, in which a single ring-shaped flap 134' extends radially inward at the distal end of the resilient seal 132' so as to cover a portion of the plunger distal end opening. The ring-shaped flap 134' is biased radially inward and is further flexible to be moved away from the plunger distal end opening and slightly into the opening in the same manner as described above for the embodiment of FIG. 7.

The plunger plug 144 includes a convex and frusto-conical surface 145 that extends toward the distal end of the barrel and engages with a generally complimentary, concave and frusto-conical cavity portion 159 of needle assembly 156 when the plunger is fully depressed into the barrel as described below. Alternatively, the end wall may be formed with any suitable outwardly or inwardly extending surface (e.g., conical, convex, V-shaped, rectangular shaped, multifaceted, etc.) or even a flat or planar surface as desired for a particular application. However, complimentary engaging surface features of the plunger plug and the needle assembly are preferred in order to minimize or eliminate open or "dead" space within the fluid cavity during removal of fluid from the fluid cavity.

At least one notch 146 can be formed on the plug at the base of the frusto-conical surface. The notch 146 can extend around the periphery of the plug at the base of the frusto-conical surface or, alternatively, consist of a single notch or one or more spaced notch sections. The notch basically serves to provide a fluid flow path between the fluid cavity within the barrel and the fluid channel in the needle assembly when the plunger is substantially or completely engages with the needle assembly. In addition, the notched plunger plug minimizes or eliminates the potential for an increase or build-up of hydraulic pressure within the fluid cavity during movement of the plunger toward the needle assembly.

Needle assembly 156 includes a needle holder or stem 158 that connects with a syringe needle 160 and is affixed within the distal end extension 126 of the barrel such that the needle 160 extends from the distal end of the barrel prior to and during use. The needle stem 158 and needle 160 preferably releasably engage with each other via any suitable fluid tight engagement. In a preferred embodiment, the releasable engagement between the needle stem and the needle is a threaded engagement, where the needle stem includes a male threaded configuration and the needle includes a female threaded connector to releasably connect with the needle stem. This connection differs from conventional syringe needle connections, such as Luer Lock configurations. In addition, this threaded configuration provides an easy, universal connection with needles of various gauges and types. However, it is noted that the needle can also be attached to the needle stem in any other suitable releasable or non-releasable manner.

A cavity 157 extends axially from a proximal end of the needle stem 158 to the connection point with the needle 160 in order to facilitate fluid communication between the needle and fluid cavity 150 within the barrel. In addition, cavity 157 includes a widened portion 159 at the proximal end of needle stem 158 that is frusto-conical in configuration and widens toward the proximal end of the barrel so as to be generally aligned and complimentary with the frusto-conical surface 145 of the plunger 130. As noted above, when the plunger is depressed toward the needle assembly, the frusto-conical surface 145 of plug 144 generally aligns and engages with widened portion 159. When the plunger plug is brought toward and fully engages widened portion 159 of the needle assembly, notch 146 defined on plug 144 ensures a fluid flow path exists between fluid cavity 150 and needle assembly cavity 157 and reduces or eliminates any build-up of hydraulic pressure within the fluid cavity.

The needle stem 158 further includes a radially extending flange 162 at its proximal end that is suitably dimensioned to engage with a step or ledge 121 disposed along an interior surface of the distal end extension 126 in order to prevent movement of the needle assembly distally beyond ledge 121 during depression of the plunger toward the distal end of the barrel.

A stem ring 164 is secured to and extends radially from the flange 162 of needle stem 158 to engage with the interior wall surface of distal end extension 126 of the barrel. The stem ring 164 is preferably formed or molded as a part of flange 162 and needle stem 158 and includes notched or scored sections 165 at the connection point of stem ring 164 and needle stem 158, where the scored sections are formed on opposing surfaces of both the needle stem flange and the stem ring. The scored sections 165 define a thin membrane or reduced material section that is torn or broken during operation of the syringe to facilitate retraction of needle assembly 156 in the manner described below. The stem ring 164 is preferably dimensioned to facilitate a partial sliding of a broken portion of the stem ring along the interior wall surface of the barrel when the plunger is depressed to engage with needle stem 158 as described below.

The diameter of the stem ring can be selected to be slightly smaller, the same size, or slightly larger than the diameter of the interior wall surface of distal end extension 126 at the location where the stem ring engages the barrel. In the present embodiment, the diameter of stem ring 164 is slightly larger in comparison to the diameter of the interior wall surface of the barrel that engages with the stem ring such that the stem ring is slightly compressed during engagement with the barrel and forms an effective fluid tight seal. The dimensions of the stem ring are further selected to provide a compression fit/fluid tight seal at the stem ring/barrel interior wall interface while facilitating a sliding of the stem ring with the barrel interior wall surface when the plunger is completely depressed within the barrel. Alternatively, it is noted that the stem ring can be connected directly to the barrel interior wall surface (e.g., via adhesive bonding, welding, etc.).

A radial protrusion or annular shoulder 166 is disposed along the interior surface and near the proximal end of the distal end extension 126 of the barrel. The shoulder 166 engages with stem ring 164 to prevent movement of the needle assembly toward the proximal end of the barrel while the stem ring remains attached with needle stem 158. A resilient member 184 (e.g., a coil spring) is disposed between the flange 162 of needle stem 158 and an interior ledge 186 disposed on the interior surface of the distal end extension 126 at a location between ledge 121 and the distal end of the barrel. When the needle assembly 156 is press fit into the distal end extension 126 of the barrel (as described below) such that stem ring 164 is extended distally beyond the radial protrusion 166 of the barrel, resilient member 184 is compressed to bias the needle assembly toward the proximal end of the barrel.

The plunger retraction cavity further includes trapping structure within the retraction cavity that, in combination with the resilient seal flaps, engages with and prevents the needle and portions of the needle assembly from exiting the retraction cavity once they have retracted within the cavity. In particular, plunger 130 includes protrusions 200 that extend from interior annular wall surfaces of the plunger in a radially inward direction within retraction cavity 148. The protrusions 200 serve as catch tabs for engaging and trapping portions of the needle and needle assembly (including resilient member) that are retracted within the cavity 148 in the manner described below. The protrusions 200 can have any suitable dimensions and extend for any selected distance along the interior wall surface of the plunger. For example, protrusions 200 can extend the entire circumference of the interior wall surface of the plunger so as to be ring shaped. Alternatively, protrusions 200 can extend only a portion of the circumference of the interior wall surface of the plunger.

Preferably, the protrusions 200 extend at a selected angle from the interior wall surface of the plunger such that the terminal or free end of the protrusions 200 extend toward the proximal end of the plunger (e.g., the protrusions 200 extend upward as shown in FIG. 2). As can be seen in the figures, two protrusions 200 are provided near the plunger distal end that extend at an angle of about 20° to about 45° from the interior wall surface of the plunger such that the free ends of the protrusions 200 extend toward the plunger proximal end. However, it is noted that the internal plunger protrusions can extend at any selected angle (e.g., 90° or less) from the plunger wall. In addition, any suitable number of protrusions (e.g., one, two, three or more) can be provided at any suitably spaced locations along interior wall surface portions of the plunger. The two protrusions 200 extend from interior wall surface portions of the plunger at generally diametrically opposed locations with respect to each other. While the embodiment of FIGS. 1-6 shows two protrusions 200 at similar location with respect to each other within the plunger, protrusions can also be provided at varying locations within the plunger and in any selected configurations. In addition, the protrusions can be provided along plunger interior wall surface portions at any selected radial wall surface location with respect to other protrusions.

The protrusions 200 are also of a selected length and extend a sufficient distance within the retraction cavity 148 so as to facilitate engagement of the protrusions with the resilient member 184 (e.g., coil spring), needle 160 and/or any other portions of the needle assembly (e.g., needle stem flange 162) that have been forced into the needle retraction cavity 148. The internal plunger protrusions preferably have a suitable flexibility and resilience to facilitate a slight flexure of the protrusions toward the plunger interior wall surface portions to which they are attached when the needle assembly is retracted into the retraction cavity, while being resistant to flexing in a direction away from the plunger interior wall surface portions beyond the angles in which they extend from the plunger interior wall at their original positions. Thus, the protrusions 200 can be designed such that they do not resist or impede movement of the needle and portions of the needle assembly (including the resilient member) during retraction within the plunger, but engage with and/or resist distal movement of the needle and/or needle assembly portions after retraction within the plunger has occurred.

Preferably, the protrusions 200 are designed such that, in combination with the resilient seal flaps, they provide a slight resistance to the needle and portions of the needle assembly (in particular, the resilient member). Like the resilient seal flaps, while the protrusions 200 do not impede retraction of the needle into the plunger retraction cavity, they provide enough resistance that they effectively reduce the retraction force caused by the resilient member and thus the velocity at which the needle and portions of the needle assembly retract into the retraction cavity. Once the needle and needle assembly portions are within the retraction cavity, the protrusions 200 preferably engage and become entangled with the resilient member to effectively prevent removal of the needle from the plunger.

The syringe 120 is designed so that complete depression of plunger 130 within barrel 122 facilitates a displacement of plunger plug 144 from the plunger and also a tearing or breaking away of the stem ring 164 from flange 162 of needle stem 158 to facilitate retraction of the needle stem and the needle 160 into the retraction cavity 148. In this embodiment, stem ring 164 of needle stem 158 includes at least one raised ridge 172 that extends from a proximal end of the needle stem and is configured to make initial contact with annular distal edge 178 of the plunger when the plunger is displaced within the barrel. While only one ridge 172 is depicted in FIGS. 1-6, it is noted that any selected number of ridges can be provided at any suitable locations and suitably spaced from each other along the proximal end of the needle stem that faces the plunger. The annular distal edge 178 of the plunger is generally planar in configuration.

Plunger resilient seal 132 is further designed and suitably dimensioned and positioned around the plunger proximate the plunger distal end such that, upon complete depression of the plunger within the barrel, distal end portions of the resilient seal engage and compresses slightly against a narrowing portion 190 of the interior barrel wall that defines a transition between main body portion 124 and distal end extension 126. The resilient seal does not slide with respect to the plunger, but rather compresses slightly against the barrel wall narrowing portion at the end of the plunger stroke that initiates needle retraction, and this serves to further minimize or eliminate "dead" space within the fluid cavity 150 as well as to displace any residual fluid from the fluid cavity into needle stem cavity 157.

The needle stem can be assembled within the syringe such that the ridge (or ridges) is aligned in any selected orientation with respect to the plunger distal end. The stem ring ridge(s), plunger and annular distal end of the plunger and needle stem are suitably dimensioned in the longitudinal direction of the syringe and further suitably aligned with each other to facilitate engagement of stem ring ridge(s) 172 and/or other proximal end surface portions of stem ring 164 with annular distal edge 178 of the plunger and plunger plug 144 with needle stem 158 upon complete depression of the plunger, which in turn facilitates a tearing or breakage of stem ring 164 from needle stem flange 158 at the scored sections 165 and a forcing of plunger plug 144 from its frictional engagement with plunger ledge 141 to initiate retraction of needle assembly 56 along with the plunger plug into retraction cavity 48 of the plunger.

In operation, the distal end of the plunger is displaced a suitable distance toward the proximal end of the barrel to draw fluid from needle 160 into fluid cavity 150. Upon injection of the needle into an injection site, the plunger is then depressed toward the distal end of the barrel to force fluid from cavity 150 and through needle 160. Referring to FIGS. 2-6, as the plunger is further depressed within the barrel, the frusto-conical surface 145 of plunger plug 144 moves into the widened portion 159 of central cavity 157 of needle stem 158 to force any remaining fluid through the needle prior to retraction (thus reducing "dead" space between the engaging portions of the plunger and needle assembly). The notch 146 on the plunger plug provides a fluid channel for fluid to continue to flow into central cavity 157 even when plunger surface 145 is substantially in contact with the widened cavity portion 159. In addition, ridge 172 of needle stem 158 initially engages a portion of annular distal edge 178 of the plunger to initiate a tearing or breaking away of stem ring 164 from needle stem 158 along the scored sections 165. Approximately contemporaneously, surface 145 of plunger plug 144 engages needle stem 158 within the widened cavity portion 159, and such continued depression of the plunger toward the needle assembly overcomes the frictional force holding the plunger plug within the plunger, forcing the plunger plug toward the proximal end of the plunger and into retraction cavity 148.

Complete depression of the plunger within the barrel further forces plunger annular distal edge 178 against other surface portions of stem ring 164, causing the portion of the stem ring that has already broken away from flange 162 to slide distally a short distance along the interior wall of the barrel so as to become oriented at a slight angle with respect to the central axis of needle stem 158. In addition, the portion of the stem ring that has not broken away is prevented from moving distally until it has become broken away from the needle stem. This sliding of the broken portion of the stem ring 164 along the interior wall of the barrel, in combination with the continued pressure applied by the fully depressed plunger to the stem ring, results in a progressive tearing or breakage of the stem ring in both directions along scored sections 165 until the stem ring is fully separated from tab 162. In addition, the forced engagement of plunger plug 144 with needle stem 158 results in further movement of the plunger plug from its frictional engagement with the distal end ledge 141 of the plunger, resulting in dislodging of the plunger plug from the plunger. Plunger resilient seal 132 compresses slightly against the narrowed portion 190 of the barrel interior wall to force residual fluid into the needle assembly, while plunger plug notch 146 provides a fluid flow path for such fluid when plunger surface 145 engages with needle stem 158 within widened cavity portion 159.

The design of the syringe can be configured such that the stem ring 164 is completely separated from needle stem 158 immediately prior to, substantially simultaneously with, or immediately after the complete dislodging of plunger plug 144 from the plunger. As shown in the series of FIGS. 2-6, the initial dislodging and axial displacement of plunger plug 144 begins just prior to initial contact between stem ring ridge 172 and plunger distal edge 178 and partial breakage of stem ring 164 from needle stem tab 162. However, the syringe can also be designed such that initial and partial breakage of the stem ring occurs prior to any initial dislodging and axial displacement of the plunger plug.

Once complete separation of the stem ring from the tab of the needle stem and at least a partial dislodging of the frictional engagement between the plunger plug and the plunger is achieved, resilient member 184 forces needle stem 158 and needle 160, along with plunger plug 144, proximally into the retraction cavity 148 within the plunger. Flaps 134 on resilient seal 132, which engage the plunger plug 144 (e.g., as shown in FIG. 2), move radially inward as the plug is released from the distal end opening in the plug and is retracted within the retraction cavity. In addition, protrusions 200 within the retraction cavity 148 are preferably configured to flex in a direction toward the interior wall surface portions of the plunger that are located between the protrusions and the plunger proximal end during contact with any portion of the needle assembly and needle so as minimize any resistance to the needle stem 158, needle 160 and resilient member 184 during retraction. The protrusions are further preferably configured to resiliently flex back to their original positions once retraction is complete. As noted above, the resilient seal flaps 134 can flex slightly inward within the plunger opening to permit movement of the retracting needle assembly components into the plunger retraction cavity, but the flaps move back to their relaxed position and obstruct the plunger opening to resist or prevent removal of the retracted needle assembly components (e.g., by engaging with resilient member 184) after such components are received within the retraction cavity.

Figure 6:
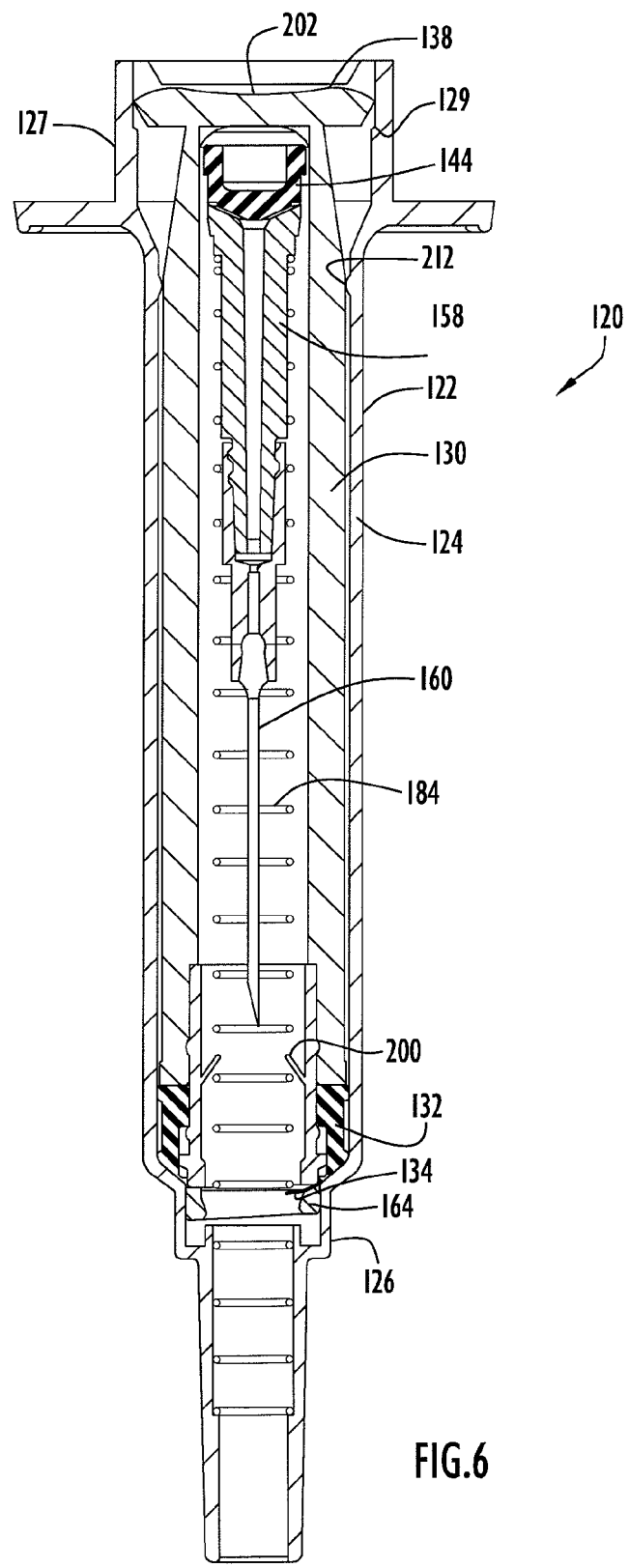
FIG. 6 is a side view in cross-section of the syringe of FIG. 14 with the needle fully retracted into the syringe after use.

As can be seen from FIG. 6, when plunger 130 has been fully depressed within barrel 122 and retraction of needle assembly 156 has occurred, flange 139 of the plunger extends slightly into the extended barrel portion 127 and is locked within annular groove 129. In this locked position, removal of the plunger from the barrel is prevented. Removal of the needle and needle assembly portions within the plunger retraction cavity 148 is also prevented by the inwardly extending protrusions 200 within the retraction cavity and also the resilient seal flaps 134 that engage with and/or limit or prevent movement of the retracted elements toward the distal end of the plunger and out of the retraction cavity.

Figure 9:
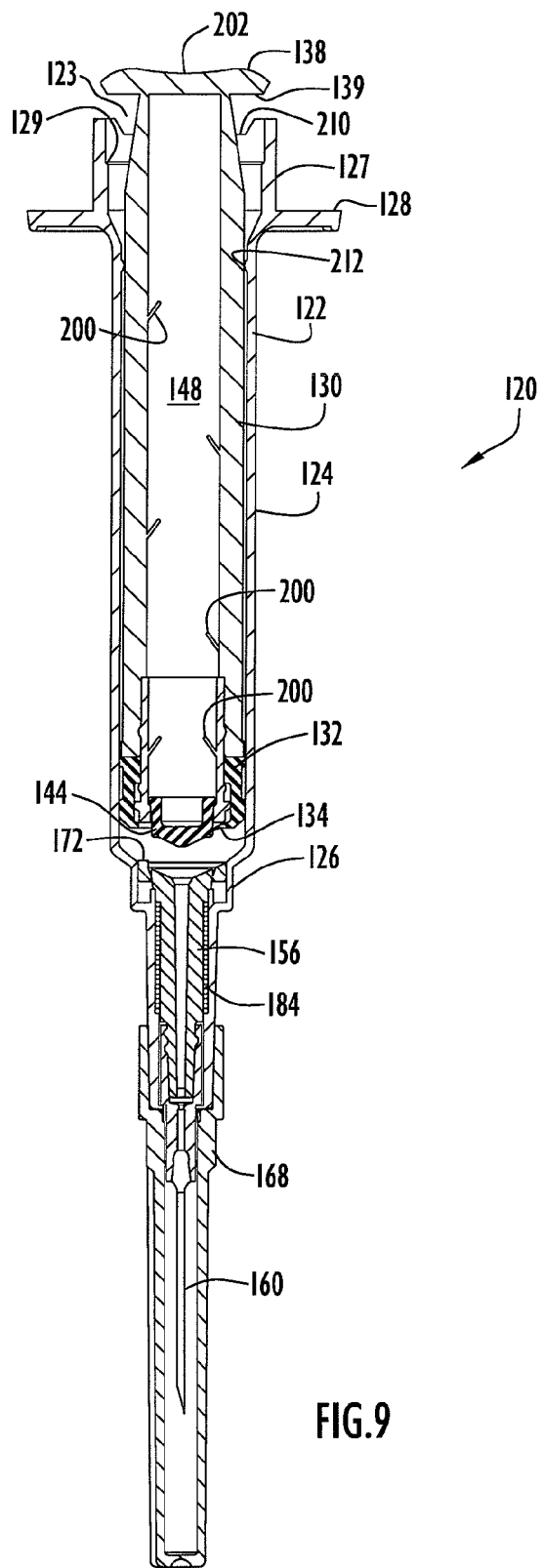
FIG. 9 is a side view in cross-section of another embodiment of a syringe in accordance with the present invention.

Another syringe embodiment is shown in FIG. 9, in which plunger 130 includes a number of inwardly extending protrusions 200 disposed within the retraction cavity 148. The protrusions 200 are disposed at varying locations along the length of the plunger, with some protrusions being spaced in a staggered manner with respect to each other. At least two protrusions are provided along the interior wall surface portions of the plunger at generally diametrically opposed positions with respect to each other. However, any other suitable placement of protrusions within the plunger retraction cavity is also possible in accordance with the present invention.

Figure 10:
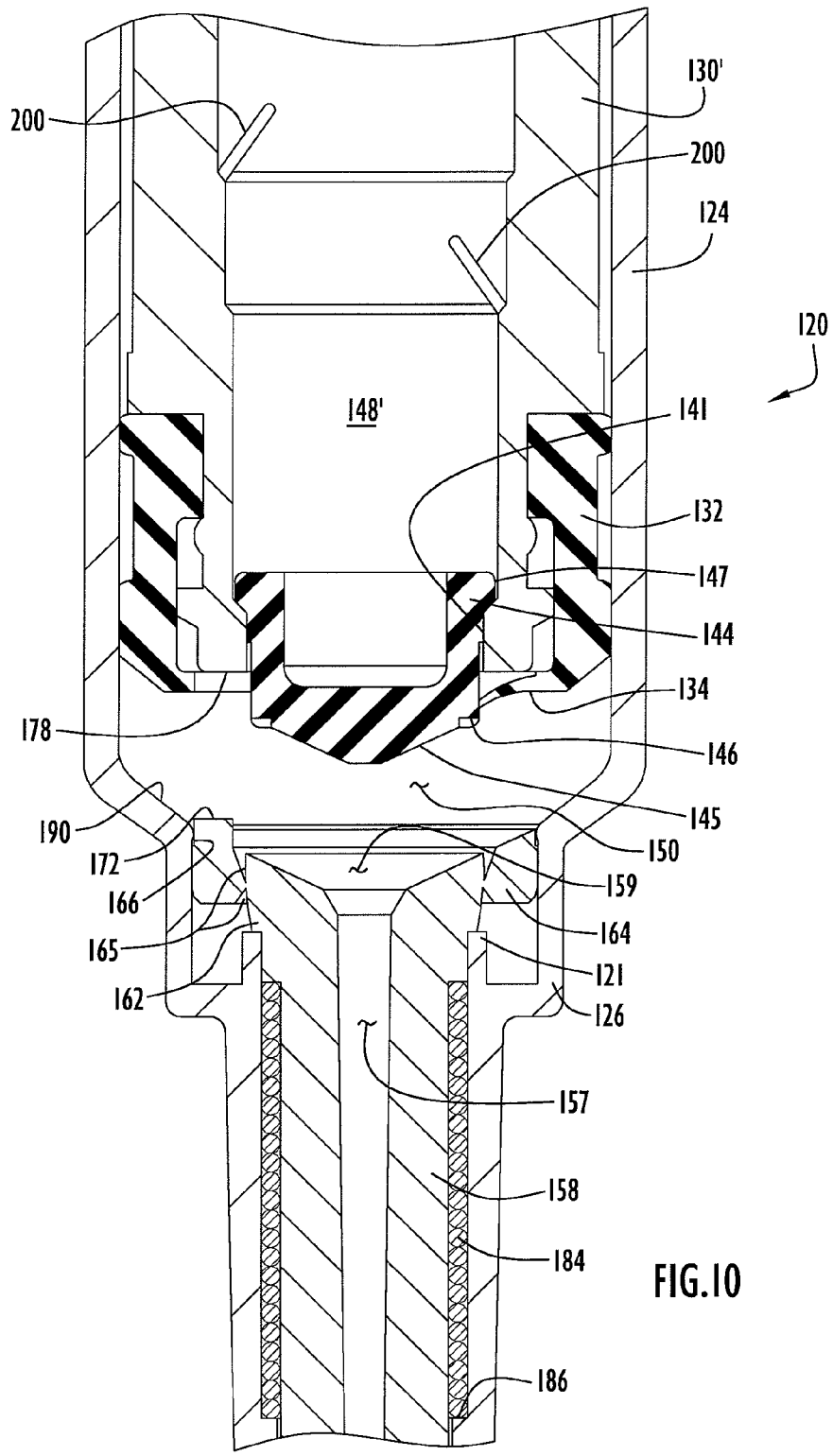
FIG. 10 is a partial side view in cross-section of a further embodiment of a syringe in accordance with the present invention.

A further embodiment of a retractable syringe with the needle trap feature provided in the plunger retraction cavity in accordance with the present invention is depicted in FIG. 10. The syringe of this embodiment is similar in design and configuration to the syringe of FIGS. 1-6, with the exception of a modification to the retraction cavity and the location of the retraction cavity protrusions. In particular, the retraction cavity 148' of plunger 130' includes a stepped contour in which the cross-sectional dimension (e.g., diameter) of the retraction cavity increases slightly in a stepped manner from the distal end of the plunger to its proximal end. A pair of protrusions 200, which are of substantially similar design and configuration as the protrusions described above for the previous embodiments, extend at opposing and vertically staggered interior plunger wall surface portions within the retraction cavity 148. A first protrusion 200 extends from an interior plunger wall surface portion at a first stepped location that defines a transition in cross-section of the plunger cavity. The second protrusion 200 extends from another interior wall surface portion that is generally diametrically opposed to the location of the first protrusion and at which a second stepped transition occurs within the plunger retraction cavity.

In the embodiment of FIG. 10, the protrusions 200 are preferably configured to slightly resist movement of the needle and portions of the needle assembly to reduce the force and velocity of the needle as it moves into the retraction cavity 148'. For example, the protrusions 200 are configured to engage with the resilient member 184 as it expands into the retraction cavity, thus reducing the biasing force of the resilient member on the needle and portions of the needle assembly. After retraction occurs, the protrusions 200 engage with the resilient member and/or other portions of the needle assembly and needle to prevent removal of the needle from the retraction cavity.

Figure 11:
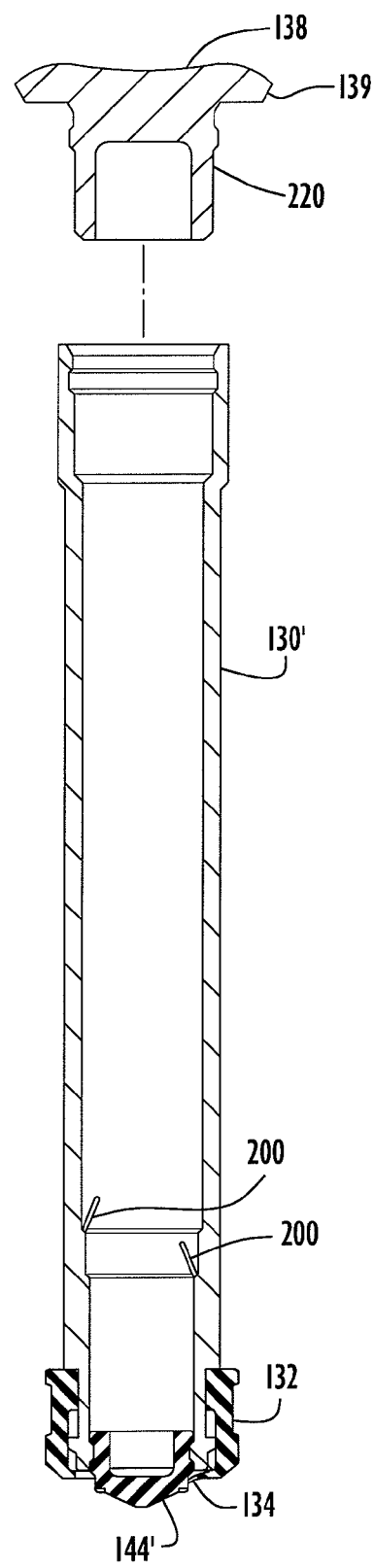
FIGS. 11 and 12 are side views in cross-section of further embodiments of plungers for use with retractable syringes in accordance with the present invention.
Figure 12:
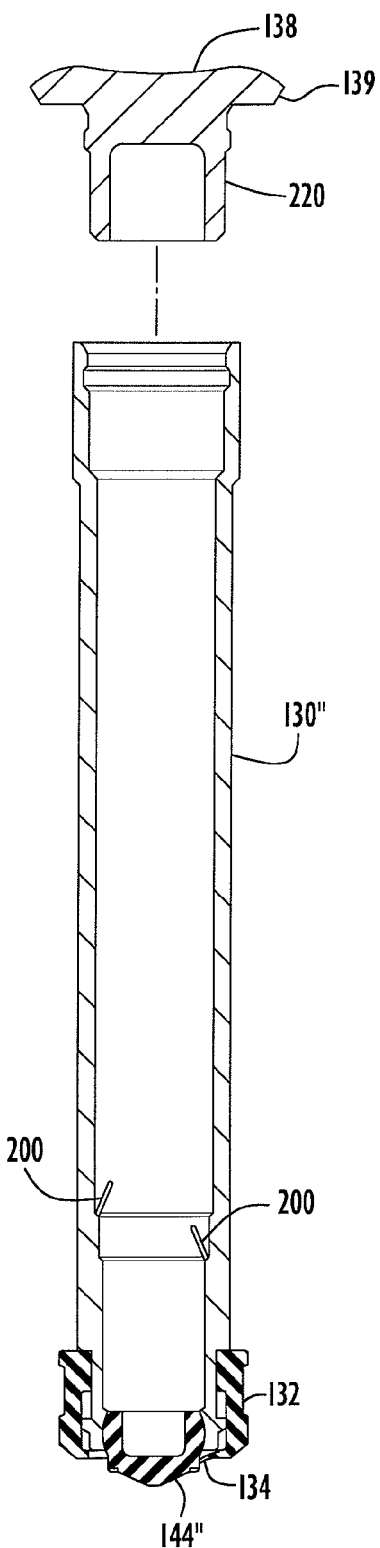

Each of the plungers 130', 130" of FIGS. 11 and 12 includes a similar stepped contour as that described above and shown in FIG. 10. Further, the plunger embodiments of FIGS. 11 and 12 are utilized in a syringe and include a needle trap configuration that is similar in design and function to that described in all of the previous embodiments. These plungers 130', 130" differ from the previous embodiments, however, in that the plunger plug is secured in a snap tight configuration at the distal end of the plunger (rather than being held solely by a frictional fitting engagement with the plunger). In particular, in the embodiment of FIG. 11, the plunger plug 144' includes a groove and the plunger includes an annular ring-like protrusion that extends radially inward within the plunger cavity and engages the plunger plug in the groove to achieve a snap tight plunger plug fit in the plunger. During retraction, the plunger plug overcomes the snap tight fit by riding over the annular protrusion until it is released to retract within the plunger cavity. In FIG. 12, the plunger plug 144" and plunger distal end include an opposite snap tight configuration, where the plunger plug includes an outwardly extending bump or ridge that engages with a groove along the interior plunger wall.

In addition, each of the plungers 130', 130" of FIGS. 11 and 12 includes a thumb cap 220 that includes thumb pad 138 and flange 139. The thumb cap 220 connected with the plunger by inserting the thumb cap into a proximal end opening of the plunger. The thumb cap further includes an annular ridge that extends from a sidewall portion of the thumb cap and fits in a snap tight fitting relationship with a corresponding groove disposed along an internal wall surface portion of the plunger so as to secure the thumb cap within the plunger. This feature facilitates the assembly of the plunger by inserting the plunger plug into the proximal end opening of the plunger and for securing at the plunger distal end opening prior to insertion and securing of the thumb cap with the plunger.

The needle trap configurations of the invention are not limited to the embodiments as described above. Rather, the use of the internal protrusions in the plunger retraction cavity can be used in any retractable syringe embodiment in which a needle is retracted within the cavity of a plunger to prevent reuse of the needle. For example, the needle trap configuration of the present invention can be employed for use in a wide variety of retractable syringe embodiments including, without limitation, the embodiments described in U.S. Pat. Nos. 5,578,011, 5,632,733, 6,090,077, and 5,935,104.

A syringe in accordance with the present invention can also be configured for use in other, needle-free applications (i.e., applications that do not include the use of needles). For example, a syringe of the present invention can be configured with a suitable connector to connect directly with an intravenous (IV) fluid line for injection of fluid from the syringe into the IV line. The retraction of the needle stem would prevent further use of the syringe after a single fluid injection.

While the invention has been described in detail and with reference to a specific embodiment thereof, it will be apparent to one skilled in the art that various changes and modifications can be made therein without departing from the spirit and scope thereof. Thus, it is intended that the present invention covers the modifications and variations of this invention provided they come within the scope of the appended claims and their equivalents.

What is claimed:

1. A syringe comprising:
a hollow barrel including an opening at a proximal end of the barrel, an opening at a distal end of the barrel and a fluid chamber disposed within the barrel;
a hollow plunger extending into the barrel via the proximal end opening of the barrel and axially movable within the barrel toward and away from the barrel distal end, wherein the plunger includes a removable plug that is frictionally fit and releasably secured to the plunger at an opening disposed at a distal end of the plunger and is movable to disengage with the plunger distal end opening during use of the syringe to facilitate access to a retraction cavity disposed within the plunger;
a resilient seal secured around an external wall portion of the plunger near the plunger distal end, wherein the resilient seal includes at least one flexible member that extends beyond the plunger distal end and is biased to at least partially cover and obstruct the plunger distal end opening when the plunger plug is disengaged from the plunger distal end opening; and
a needle assembly secured within and at the barrel distal end, the needle assembly including a needle holder with a connector to secure a needle to the needle holder so as to permit the needle to extend through the distal end opening of the barrel;
wherein the needle holder is biased toward the proximal end of the barrel and is configured to be forced into the retraction cavity of the plunger upon complete depression of the plunger distally within the barrel, and the plunger includes at least one protrusion that extends from an internal wall surface of the plunger within the retraction cavity and is configured to engage with and limit or prevent movement of portions of the needle assembly that have been forced into the retraction cavity.

2. The syringe of claim 1, wherein the plunger includes a plurality of the protrusions extending within the retraction cavity and configured to engage with and limit or prevent movement of the portions of the needle assembly that have been forced into the retraction cavity, at least two of the protrusions being located at longitudinally spaced locations of the plunger.

3. The syringe of claim 2, wherein the retraction cavity includes at least two cavity sections having different transverse cross-sectional dimensions.

4. The syringe of claim 3, wherein at least one of the protrusions is located at a stepped internal wall surface portion that defines a transition between the two cavity sections.

5. The syringe of claim 1, wherein the at least one protrusion is configured to flex in a direction toward an interior wall surface portion of the plunger that is located between the protrusion and a proximal end of the plunger when contacted by one or more portions of the needle assembly that have been forced into the retraction cavity.

6. The syringe of claim 1, wherein the at least one flexible member includes a plurality of flexible flaps that extend radially inward over portions of the plunger distal end opening when the plunger plug is disengaged from the plunger distal end opening.

7. A hollow plunger for use in a retractable syringe, the syringe comprising a hollow barrel including an opening at a proximal end of the barrel, an opening at a distal end of the barrel and a fluid chamber disposed within the barrel, and a needle assembly secured within and at the distal end of the barrel, the needle assembly including a needle holder with a connector to secure a needle to the needle holder so as to permit the needle to extend through the distal end opening of the barrel, wherein the plunger is configured to extend into and axially move within the barrel toward and away from the barrel distal end, the plunger comprising:
  a removable plug that is frictionally fit and releasably secured to the plunger at an opening disposed at a distal end of the plunger and is movable to disengage with the plunger distal end opening during use of the syringe to facilitate access to a retraction cavity disposed within the plunger, wherein the needle holder is biased toward the proximal end of the barrel and is configured to be forced into the retraction cavity of the plunger upon complete depression of the plunger distally within the barrel;
  a resilient seal secured around an external wall portion of the plunger near the plunger distal end, wherein the resilient seal includes at least one flexible member that extends beyond the plunger distal end and is biased to at least partially cover and obstruct the plunger distal end opening when the plunger plug is disengaged from the plunger distal end opening; and
  at least one protrusion that extends from an internal wall surface of the plunger within the retraction cavity and is configured to engage with and limit or prevent movement of portions of the needle assembly that have been forced into the retraction cavity.

8. The plunger of claim 7, wherein the plunger includes a plurality of the protrusions extending within the retraction cavity and configured to engage with and limit or prevent movement of portions of the needle assembly that have been forced into the retraction cavity, at least two of the protrusions being located at longitudinally spaced locations of the plunger.

9. The plunger of claim 8, wherein the retraction cavity includes at least two cavity sections having different transverse cross-sectional dimensions.

10. The plunger of claim 8, wherein at least one of the protrusions is located at a stepped internal wall surface portion that defines a transition between the two cavity sections.

11. The plunger of claim 7, wherein the at least one protrusion is configured to flex in a direction toward an interior wall surface portion of the plunger that is located between the protrusion and a proximal end of the plunger when contacted by one or more portions of the needle assembly that have been forced into the retraction cavity.

12. The plunger of claim 7, wherein the at least one flexible member includes a plurality of flexible flaps that extend radially inward over portions of the plunger distal end opening when the plunger plug is disengaged from the plunger distal end opening.

13. A method of using a retractable syringe, the syringe comprising a hollow barrel including an opening at a proximal end of the barrel, an opening at a distal end of the barrel and a fluid chamber disposed within the barrel, a hollow plunger extending into the barrel via the proximal end opening of the barrel and axially movable within the barrel toward and away from the barrel distal end, the plunger including a removable plug that is frictionally fit and releasably secured to the plunger at an opening disposed at a distal end of the plunger and a retraction cavity with at least one protrusion extending from an internal wall surface of the plunger within the retraction cavity, a resilient seal secured around an external wall portion of the plunger near the plunger distal end, the resilient seal including at least one flexible member that extends beyond the plunger distal end and is biased to at least partially cover and obstruct the plunger distal end opening when the plunger plug is moved to disengage from the plunger distal end opening, and a needle assembly secured within and at the barrel distal end, the needle assembly including a needle holder with a connector to secure a needle to the needle holder so as to permit the needle to extend through the distal end opening of the barrel, the needle holder being biased toward the proximal end of the barrel, the method comprising:
  facilitating aspiration of fluid through the needle and into the fluid chamber within the barrel by moving the distal end of the plunger toward the proximal end of the barrel;
  facilitating withdrawal of the aspirated fluid from the fluid chamber within the barrel by moving the distal end of the plunger toward the distal end of the barrel;
  facilitating retraction of portions of the needle assembly including the needle holder and the needle within the retraction cavity defined within the plunger upon complete movement of the plunger into the barrel such that the needle holder contacts and disengages the plunger plug from the plunger distal end opening to permit the needle holder and needle to retract into the retraction cavity;
  facilitating engagement of the at least one protrusion and portions of the needle assembly retracted within the retraction cavity to minimize or prevent the removal of the portions of the needle assembly from the retraction cavity; and
  obstructing the plunger distal end opening, via the at least one flexible member of the resilient seal, to minimize or prevent removal of the retracted portions of the needle assembly from the retraction cavity.

14. The method of claim 13, wherein the plunger includes a plurality of the protrusions extending within the retraction cavity to engage with the retracted portions of the needle assembly.

15. A syringe comprising:
  a hollow barrel including an opening at a proximal end of the barrel, an opening at a distal end of the barrel and a fluid chamber disposed within the barrel;
  a hollow plunger extending into the barrel via the proximal end opening of the barrel and axially movable within the barrel toward and away from the barrel distal end, wherein the plunger includes a removable plug that is frictionally fit and releasably secured to the plunger at an opening disposed at a distal end of the plunger and is movable to disengage with the plunger distal end opening during use of the syringe to facilitate access to a retraction cavity disposed within the plunger;
  a resilient seal secured around an external wall portion of the plunger near the plunger distal end, wherein the resilient seal includes at least one flexible member that extends beyond the plunger distal end and is biased to at least partially cover and obstruct the plunger distal end opening when the plunger plug is disengaged from the plunger distal end opening; and a needle assembly secured within and at the barrel distal end, the needle assembly including a needle holder with a connector to secure a needle to the needle holder so as to permit the needle to extend through the distal end opening of the barrel;

wherein the needle holder is biased toward the proximal end of the barrel and is configured to be forced into the retraction cavity of the plunger upon complete depression of the plunger distally within the barrel.

16. The syringe of claim 15, wherein the at least one flexible member includes a plurality of flexible flaps that extend radially inward over portions of the plunger distal end opening when the plunger plug is disengaged from the plunger distal end opening.

17. A syringe comprising:

a hollow barrel including an opening at a proximal end of the barrel, an opening at a distal end of the barrel and a fluid chamber disposed within the barrel;

a hollow plunger having a retraction cavity and a distal end extending into the barrel via the barrel proximal end opening and axially movable within the barrel toward and away from the barrel distal end, wherein the plunger includes an opening disposed at the distal end and configured to facilitate access to the retraction cavity;

a resilient seal disposed around an external wall portion of the plunger near the plunger distal end; a needle assembly disposed within and at the barrel distal end, the needle assembly including a needle holder connector configured to secure a needle so as to permit the needle to extend through the barrel distal end opening, wherein the needle holder is configured to be biased into the plunger retraction cavity upon depression of the plunger distally within the barrel; and a member configured to at least partially obstruct the plunger opening in response to the retraction of the needle holder into the retraction cavity, wherein the member is biased toward the plunger opening and directly coupled to the plunger distal end before retraction of the needle holder into the retraction cavity.

18. The syringe as specified in claim 17 wherein the member is configured to be positioned over the plunger opening upon retraction of the needle holder into the retraction cavity.

19. The syringe as specified in claim 17 wherein the member is comprised of at least one flexible member.

20. The syringe as specified in claim 17 wherein the member comprises a plurality of flexible members.

21. The syringe as specified in claim 17 wherein the member extends beyond the plunger distal end.

* * * * *